(12) United States Patent
Åklint et al.

(10) Patent No.: US 9,545,669 B2
(45) Date of Patent: Jan. 17, 2017

(54) LAYERED MANUFACTURING OF FREE-FORM MULTI-MATERIAL MICRO-COMPONENTS

(75) Inventors: Thorbjörn Åklint, Vastra Frolunda (SE); Elis Carlstrom, Landvetter (SE); Per Johander, Hisings Backa (SE); Elisabeth Johander, legal representative, Hisings Backa (SE); Johanna Stiernstedt, Vastra Frolunda (SE)

(73) Assignee: Digital Metal AB, Höganäs (SE)

( * ) Notice: Subject to any disclaimer, the term of this patent is extended or adjusted under 35 U.S.C. 154(b) by 272 days.

(21) Appl. No.: 14/241,042

(22) PCT Filed: Aug. 22, 2012

(86) PCT No.: PCT/EP2012/066339
§ 371 (c)(1),
(2), (4) Date: May 13, 2015

(87) PCT Pub. No.: WO2013/030064
PCT Pub. Date: Mar. 7, 2013

(65) Prior Publication Data
US 2015/0306664 A1    Oct. 29, 2015

(30) Foreign Application Priority Data
Aug. 26, 2011    (SE) ...................................... 1100624

(51) Int. Cl.
*B22F 3/00*    (2006.01)
*B28B 1/00*    (2006.01)
(Continued)

(52) U.S. Cl.
CPC ........... *B22F 3/008* (2013.01); *A61C 13/0013* (2013.01); *A61C 13/0018* (2013.01); *B22F 3/22* (2013.01); *B22F 5/00* (2013.01); *B22F 5/10* (2013.01); *B28B 1/001* (2013.01); *B29C 67/0081* (2013.01); *C22C 29/12* (2013.01);
(Continued)

(58) Field of Classification Search
CPC ............. B22F 3/008; B22F 5/00; B22F 1/001
See application file for complete search history.

(56) References Cited

U.S. PATENT DOCUMENTS 6,146,567 A    11/2000 Sachs et al.
6,363,606 B1    4/2002 Johnson, Jr. et al.
(Continued)

FOREIGN PATENT DOCUMENTS

WO    WO9856566    12/1998
WO    WO03055628    7/2003

*Primary Examiner* — Rebecca Lee
(74) *Attorney, Agent, or Firm* — Lowe Graham Jones PLLC (57) ABSTRACT

The present invention relates to layer manufacturing, more particularly to a method for additive layer manufacturing of objects comprised of more than one material with free-form capability for all included materials. The invention can for example be used for producing packaging for Microsystems where the ceramic acts as an insulator and the secondary material is used to produce electrical or optical 3D conductor lines or electrical or optical 3D vias. The fine powder used in this method enables it to be used for building components with small feature size and demand for high precision. Other intended uses for this method is to build small mechanical precision parts or grinding tools, dental objects or medical implants.

20 Claims, 5 Drawing Sheets

(51) Int. Cl.
  *B29C 67/00* (2006.01)
  *C22C 29/12* (2006.01)
  *B22F 3/22* (2006.01)
  *B22F 5/10* (2006.01)
  *A61C 13/00* (2006.01)
  *H05K 3/46* (2006.01)
  *H05K 1/02* (2006.01)
  *H05K 3/12* (2006.01)
  *C22C 5/06* (2006.01)
  *B22F 5/00* (2006.01)
  *H05K 1/03* (2006.01)
  *B33Y 10/00* (2015.01)
  *B33Y 40/00* (2015.01)

(52) U.S. Cl.
  CPC ......... *H05K 1/0272* (2013.01); *H05K 1/0274* (2013.01); *H05K 3/1208* (2013.01); *H05K 3/4667* (2013.01); *B22F 2005/001* (2013.01); *B22F 2999/00* (2013.01); *B33Y 10/00* (2014.12); *B33Y 40/00* (2014.12); *C22C 5/06* (2013.01); *H05K 1/0306* (2013.01); *H05K 2201/09981* (2013.01); *H05K 2203/013* (2013.01); *H05K 2203/0126* (2013.01); *H05K 2203/122* (2013.01)

(56) References Cited

U.S. PATENT DOCUMENTS

2006/0071367 A1  4/2006  Hunter et al.
2009/0004381 A1  1/2009  Fujisawa et al.

LAYERED MANUFACTURING OF FREE-FORM MULTI-MATERIAL MICRO-COMPONENTS

PRIORITY CLAIM

This invention claims priority from PCT Application Ser. No. PCT/EP2012/066339 filed Aug. 22, 2012, which claims priority to Swedish Application Ser. No. 1100624-4 filed Aug. 26, 2011, which is hereby incorporated by reference.

FIELD OF THE INVENTION

The present invention relates to layer manufacturing, more particularly to a method for additive layer manufacturing of objects comprised of more than one material with free-form capability for all included materials.

The invention deals with a method to fabricate objects by starting with a virtual 3D model (CAD-model) and using this information to add material in a controlled manner to shape the object. These types of methods are commonly referred to by a number of terms for example rapid prototyping, free-form fabrication, layer manufacturing and additive manufacturing. 3D-printing is one method that belongs to this group. Since objects with very complex shapes can be described by a set of planar layers this method makes it possible to fabricate any desired shape within the precision of the actual implementation of these layered manufacturing methods.

BACKGROUND ART 3D-printing is a method where a powder layer is distributed on a surface. An inkjet printer is used to distribute a binder on the surface to create a temporary bond between the particles. The binder is dried and the process is repeated until a powder bed containing an object bound together with the binder is created. The lose powder is rinsed or cleared from the object and the object is then sintered. The boundaries between the original powder layers disappear and a solid object is created.

Advantages with 3D printing compared to other layer manufacturing methods are the high speed, no need to build support structures and that the final object is homogenous without residual stresses. The high speed comes from the deposition of the powder layer in one step and that the binder can be deposited with several nozzles simultaneously. Other methods that can build objects by dispensing at each point or use a single laser or electron beam spot for selective solidification are inherently slower since they can only build at one point at a time. The powder bed supports the structure making it possible to build structures containing arches without building a separate support structure that has to be removed in a later step. The powder can be deposited without density gradients and this secures that the sintering done in a separate stage can create homogenous object without differential shrinkage.

In the original 3D-printing invention (Cima U.S. Pat. No. 6,146,567) the powder was applied on the surface by spraying a suspension. In a later invention by Fcubic the powder is spread in the dry form to create a layer (Fcubic WO03055628). The latter method is very fast but it is limited to coarser powders with approximately 10-20 μm particle size that can be spread homogenously in the dry state. Finer powders, this includes most sinterable ceramic powders and hard metal powders, are impossible to spread in the dry state in a homogenous thin layer due to van der Waals attraction that inhibits the flow of dry small particles.

Microsystems are increasingly used to make products smarter, that is to add new functionally to products. They are for example used in products like solar cells, batteries, OLED, microwave components, lab-on-a chip and high temperature sensors, vehicles and kitchen appliances. Microsystems can contain sensors that sense (acceleration, radiation, force, pressure, moisture, chemical environment etc) they can also contain actuators based on electrostatic, magnetostrictive, piezoelectric and other principles.

To date it has not been possible to use layered manufacturing to directly fabricate Microsystems packaging with true 3D structures. Available methods such as LTCC (low temperature cofired ceramics) can only supply flat substrates where the electronic connection (vias) have to be placed perpendicular to the layers. This often makes it necessary to combine LTCC structures with other 3D-structures manufactured separately. Using additive and direct manufacturing to build the package would create a competitive advantage. Developing of integrated electronic chips is a very efficient streamlined production process done by silicon foundries. The packaging is however not standardized in the same way. Packaging is often the major cost in production of Microsystems. Further design, fabrication and testing of packaging are very time consuming processes.

The electrical interconnects for Microsystems are built with an insulating and an electrically conducting material. For some applications other materials are required to build resistors and to modify the dielectric properties. For optical interconnects, other material combinations are required to build waveguides. This requires that the fabrication process can build with and integrate several materials. This has not been possible in previously available methods for layered manufacturing.

SUMMARY OF THE INVENTION

In view of the above-mentioned and other drawbacks of the prior art, a general object of the present invention is to provide manufacturing of 3D-objects containing several materials with additive layered manufacturing. The invention enables efficient production of objects consisting of a powder based material (such as a ceramic, glass, hybrid, intermetallic, hard metal or metal material) but with additions of one or more secondary materials (such as a ceramic, glass, hybrid, intermetallic, hard metal or metal material). The secondary material can be integrated with freeform capability.

According to an aspect of the present invention, it relates to a method for additive layer manufacturing of objects comprised of more than one material with free-form capability for all included materials, which method comprises providing a flat substrate as a platform for building the object, hydrophobizing selected parts of a flat substrate by applying a hydrophobic solution, spreading a water-based powder suspension comprised of particles with a size below 5 μm in a layer with a thickness below 50 μm, applying a binder to the parts of the powder layer that should be retained in the shaped powder body, applying one or more secondary materials as powder suspensions or powder pastes to the gaps in the layer created by the hydrophobic repulsion of the water-based suspension, repeatedly adding powder layers, hydrophobic areas, binders and secondary materials as above to build a powder body of the desired shape and size, rinsing or clearing the object from lose powder and removing the object from the support, and performing thermal treatment to remove the binder and sinter the powder object to a solid body.

According to various exemplifying embodiments, a flat support is provided as a platform to build the object. A fine powder is deposited as a water-based suspension on the support using a slot die, doctor blade or extrusion method. A temporary binder is used to bind parts of the layer that should be included in the final shaped object. The water dries off rapidly from the concentrated suspension to solidify the layer. Several layers are deposited on top of each other to build the object with addition of a binder. A hydrophobic material is deposited selectively on each powder layer to create gaps in the next layer. The hydrophobic parts repel the water-based suspension. These gaps are filled with secondary materials using inkjet printing or dispersing. The deposition of powder layers and secondary materials is repeated with a desired number of layers. When the entire object is built, the lose powder, e.g. powder not bound together with the temporary binder, is rinsed or cleared from the object. The object is removed from the support prior to or after the rinsing or clearing from lose powder. The object is then heated to remove the temporary binder followed by further heating to sinter the object to a solid component containing several materials.

In this way structures of secondary material with an arbitrary shape can be included in the object. These structures can for example be used to build 3D vias (electrically, optically or thermally conducting lines of an arbitrarily shape and direction) in an insulating or refractive matrix.

Generally, other objectives, features, and advantages of the present invention will appear from the following detailed disclosure, from the attached dependent claims as well as from the drawings are equally possible within the scope of the invention.

BRIEF DESCRIPTION OF THE DRAWINGS

Embodiments of the invention will now be described, by way of example, with reference described exemplifying embodiments, experiments and to the accompanying drawings, wherein.

DETAILED DESCRIPTION OF THE PREFERRED EMBODIMENT

It should be understood that the drawings are not true to scale and, as is readily appreciated by a person skilled in the art, dimensions other than those illustrated in the drawings are equally possible within the scope of the invention. According to various embodiments, the invention can be used for producing packaging for Microsystems where the ceramic acts as an insulator and the secondary material is used to, or forms, 3D conductor lines or 3D vias. The fine powder used in this method makes it possible to be used, or enables, for building components with small feature size, high precision, and/or demand for high precision. Other intended uses for this method is to build optoelectronic systems, microfluidic systems, small mechanical precision parts, grinding tools, dental objects or medical implants. Microsystems formed according to various embodiments according to the invention may advantageously be used to make products smarter, that is to add new functionally to products.

The invention builds on the concept of 3D-printing. But instead of spreading or spraying a dry powder the powder layer is added as a concentrated suspension in water. The suspension is applied in a thin layer using a slot die, a doctor blade, extrusion deposition or other techniques for spreading the suspension. This is different from spraying were the ceramic or metal has to be in a very dilute suspension in order to have a viscosity to pass through the spraying nozzle. With application of a suspension with a slot die it is possible to add a very thin powder layer (1-50 µm) in a precisely controlled manner from a highly concentrated suspension. The term highly concentrated is here used to describe a suspension near the theoretical random close packing concentration. The highly concentrated suspension rapidly solidifies as it only takes the removal of a minute quantity of water to convert it into a solid. A binder is then printed on parts of the layer that should remain in the final body.

Figure 1:
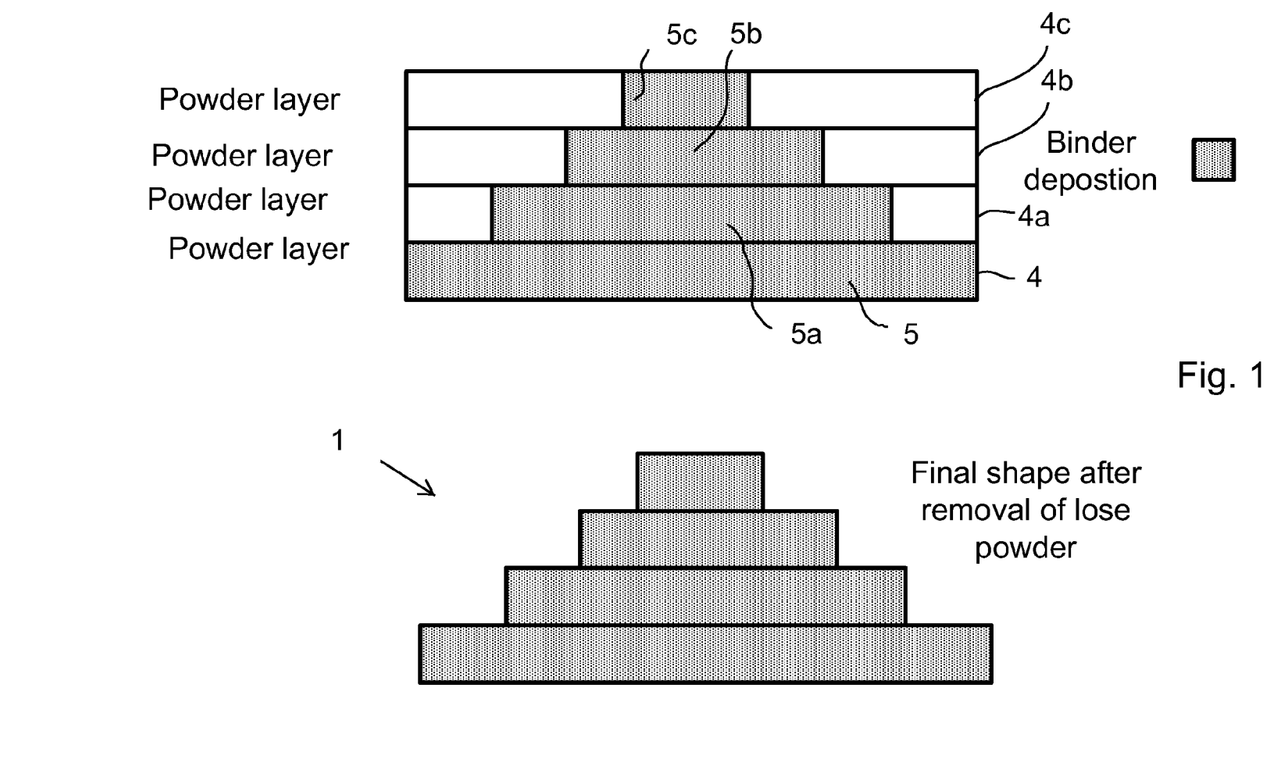
FIG. 1 is a schematic view illustrating the addition of binder to shape a structure and removal of lose powder according to an embodiment of the present invention.
Figure 2:
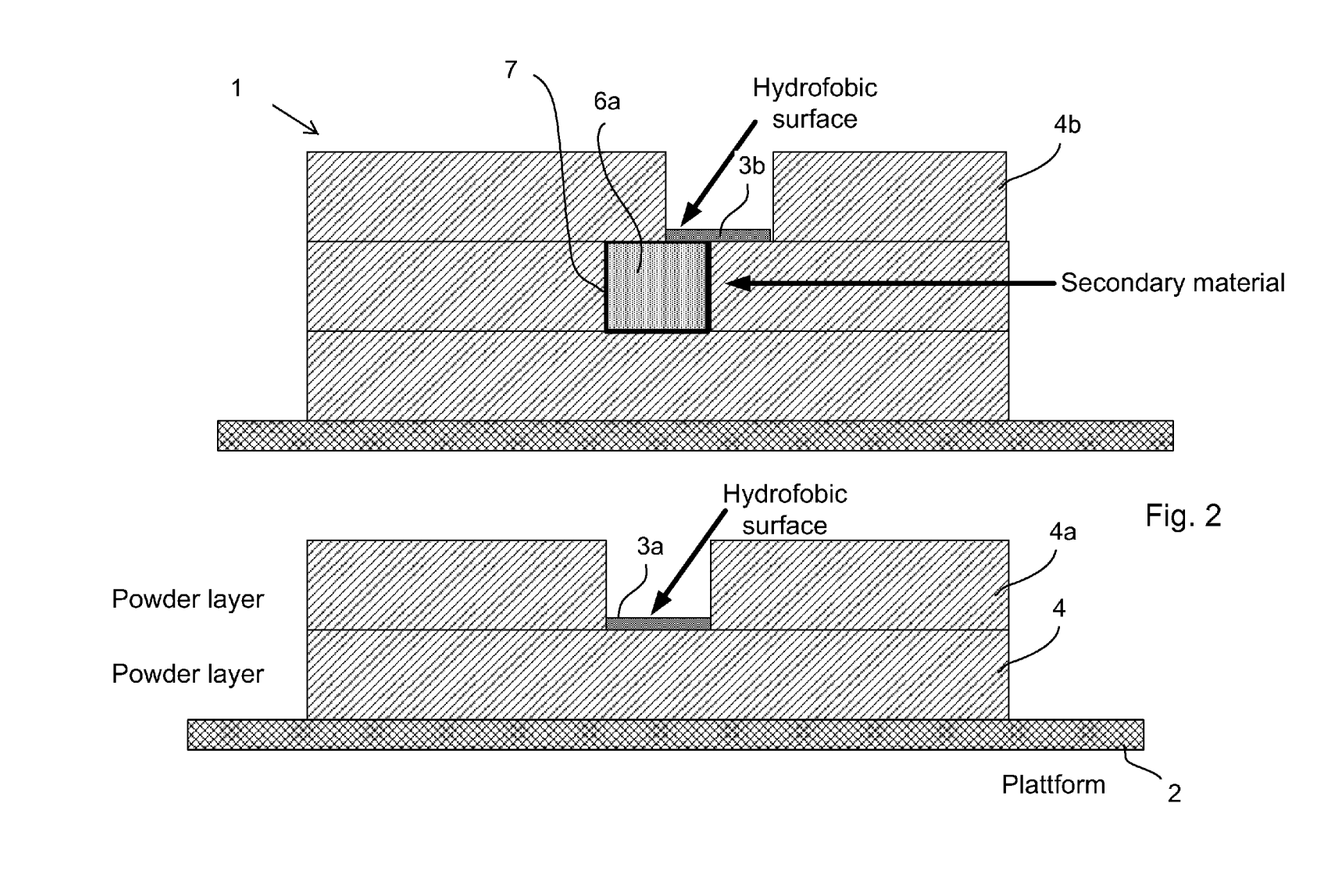
FIG. 2 is a schematic view illustrating the principle of creating gaps in layer to be filled with a secondary material according to an embodiment the present invention.

The addition of a binder to shape the structure by removing lose powder by rinsing or clearing is illustrated by FIG. 1. The principle of creating gaps in layers to be filled with a secondary material is illustrated by FIG. 2.

The material added as layers can be a ceramic but it is also possible to spread layers of other fine powders such as glass, hybrid materials, cemented carbides, intermetallics or metals. The requirement is that the powders have a low particle size, such as <5 µm, so that they can be dispersed with reduced, or without, sedimentation but also to be able to work with thin layers to make it possible to form small shapes with high precision. The powders may further be dispersed in water with reduced, or without, significant reaction between the fine powder and the water. Furthermore, according to the method, the powder may be sintered to a dense final material. For this purpose, fine non-agglomerated powders with sintering ability are utilized, wherein the particle size requirement depends on the actual type of material. For high performance ceramics a particle size below 1 µm may be utilized.

3D-printing processes can be arranged to create internal cavities (holes or channels) in a component as long as they are connected to the surface of the component and can be rinsed or cleared from lose powder after the component is created. To fill created cavities with a secondary material after manufacturing of the entire component is difficult and unpractical. To be able to add a second material inside the component may be useful, or necessary, in order to create the space for it as the layer is created.

To use mechanical drilling or laser machining to create cavities in each layer is possible but would cause emission of chips or other debris. This would be very difficult to remove and would destroy a process that aims at small structures created with high precision and high quality.

Instead of machining a hydrophobic liquid is printed selectively on part of a layer. When the next layer is added the hydrophobic areas repel the water-based powder suspension causing a gap (hole of cavity) in the layer where a second (or third or fourth material can be added). The hydrophobic liquid can for example comprise, or consist of, hydrocarbons (alkanes, oils fats), fluorocarbons or silicones.

Since the cavities are created layer by layer they can be filled layer by layer with a paste of a secondary material using dispensers, inkjet printing or other application methods. The filling of cavities with a dispenser (done at one point a time) is a slower process than the inkjet printing of the binder (done with an array of nozzles) but in most applications the area that has to be filled is only a small portion of the entire section of the component. In this way the main advantage of depositing and solidifying entire layers rapidly is maintained.

This process enables the creation of 3-dimensional via holes (3-D conductive connections or optical vias) inside of the component or to integrate other 3D structures of a second material in the structure. The added materials may be chosen or be adapted to be compatible with the sintering procedure. This problem, however, is solved for example in the commercially available LTCC technology (low temperature co fired ceramics for electronics applications).

According to an embodiment, the process can also be used with adding a sacrificial material as secondary material in the gaps created by the hydrophobic areas. The sacrificial material is chosen to temporary fill the gaps but to disappear during heat treatment prior to sintering or during the early stages of sintering. This can be used to include channels, closed channels and/or cavities in the component. Since these cavities are not filled with permanent secondary material they do not have to be connected to the outside surface of the body. The sacrificial material breaks down/evaporates through the pores of object before they are sealed during sintering. One example of a sacrificial material is graphite that oxidizes to form carbon dioxide if the object is heated in air during heat treatment. Another example of a sacrificial material is a wax that melts and evaporates during heat treatment. Rinsing or clearing of small channels or small cavities is often difficult and time consuming even if the channels or cavities are open to the surface of the object.

It is also possible with this method to add planar conductor lines by inkjet with a conductive metallic ink before the next ceramic layer is added in a similar manner as done in the LTCC technology.

For example, the method enables fabrication of ceramic packaging (or ceramic interconnects) for a wide range of Microsystems. To add functional materials and to connect this material by electric conductors makes it possible to add sensors or actuators. Adding conductor lines, resistors, inductances and capacitances and connection points for electronic chips opens for smart system integration. Microsystems may for example be used in products like solar cells, batteries, OLED, microwave components, lab-on-a chip and high temperature sensors, vehicles and kitchen appliances. Microsystems can further contain sensors that sense (acceleration, radiation, force, pressure, moisture, chemical environment etc) they can also contain actuators based on electrostatic, magnetostrictive, piezoelectric and other principles. Microsystems can also contain cavities that form waveguides for light and microwaves, as well as channels for transport of fluids. Microsystems formed according to the method may also contain optical waveguides.

The high precision and capability to build complex features and integrate secondary materials gives the possibility to fabricate small complex machining tools or medical implants as well as dental products. The method also gives the possibility to create channels and cavities with internal metallization. Such structures can be used as wave guides in microwave applications. For high frequency microwave (THz or near THz) microstrip connections needs to be replaced with wave guides. These waveguides (metalized channels) need to be of high precision and with low surface roughness to avoid losses. Such high precision and low surface roughness can be manufactured with this method.

Example 1

Figure 3:
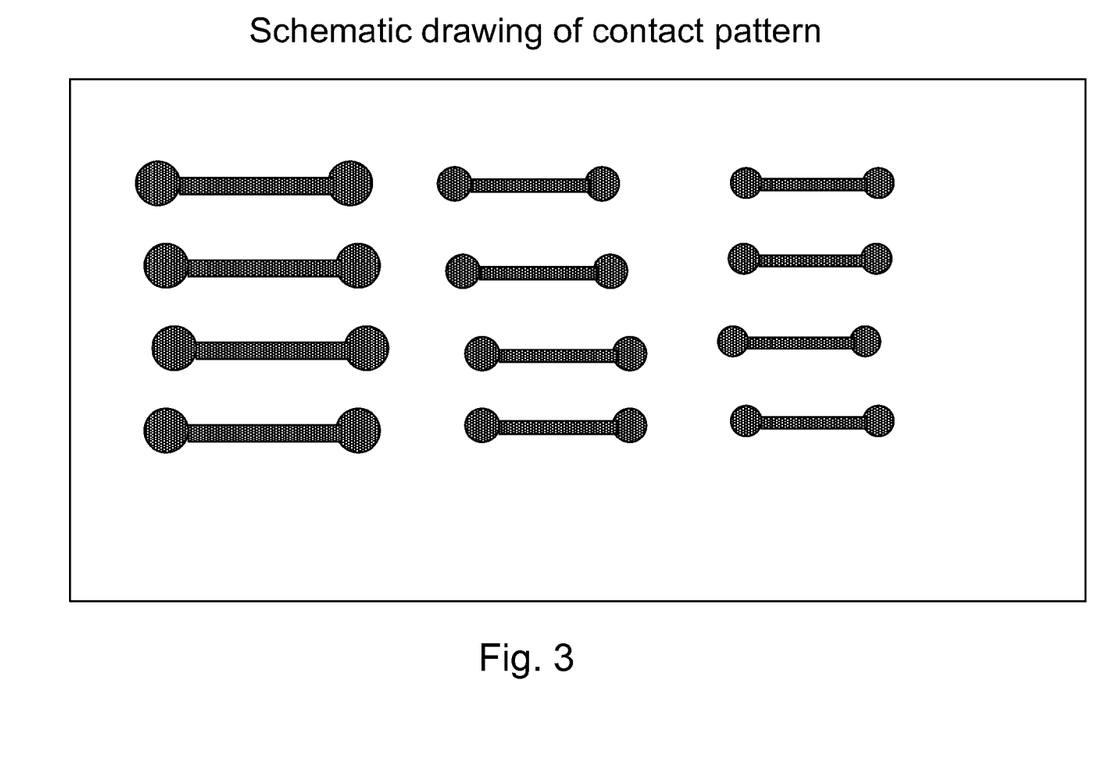
FIG. 3 is a schematic view of a contact pattern according to an embodiment of the present invention.

In a simple model experiment a doctor blade casting station was used instead of slot die for manual application of layers. On a plate of sintered alumina a metallic pattern was screen printed. The pattern consisted of straight conductor lines in different dimensions finished by a contact point, FIG. 3. Printing was done with a silver paste to have good electrical conduction.

The plate with the conductor was placed in the casting station. An alumina suspension (40 vol % AKP 30, Sumitomo Chemicals), in water with a dispersing agent (0.35% Dolapix PC21) was cast with a doctor blade with 80 μm gap. This casting created a film with fine alumina powder on the plate.

Holes for vias were created by dispensing of a hydrophobic liquid. The hydrophobic liquid was a fluorocarbon based liquid. On areas where the hydrophobic liquid was applied the alumina water-based suspension did not wet and thus it avoided those areas. Holes are created that penetrate the dry alumina powder layer.

A new layer of conductors was screen printed on top of the dried ceramic layer. The second layer conductive pattern is displaced so that the first layer can connect through the contact point. Silver paste penetrates through the created holes and connects the first layer with the second layer, thus establishing a via connection.

Figure 4:
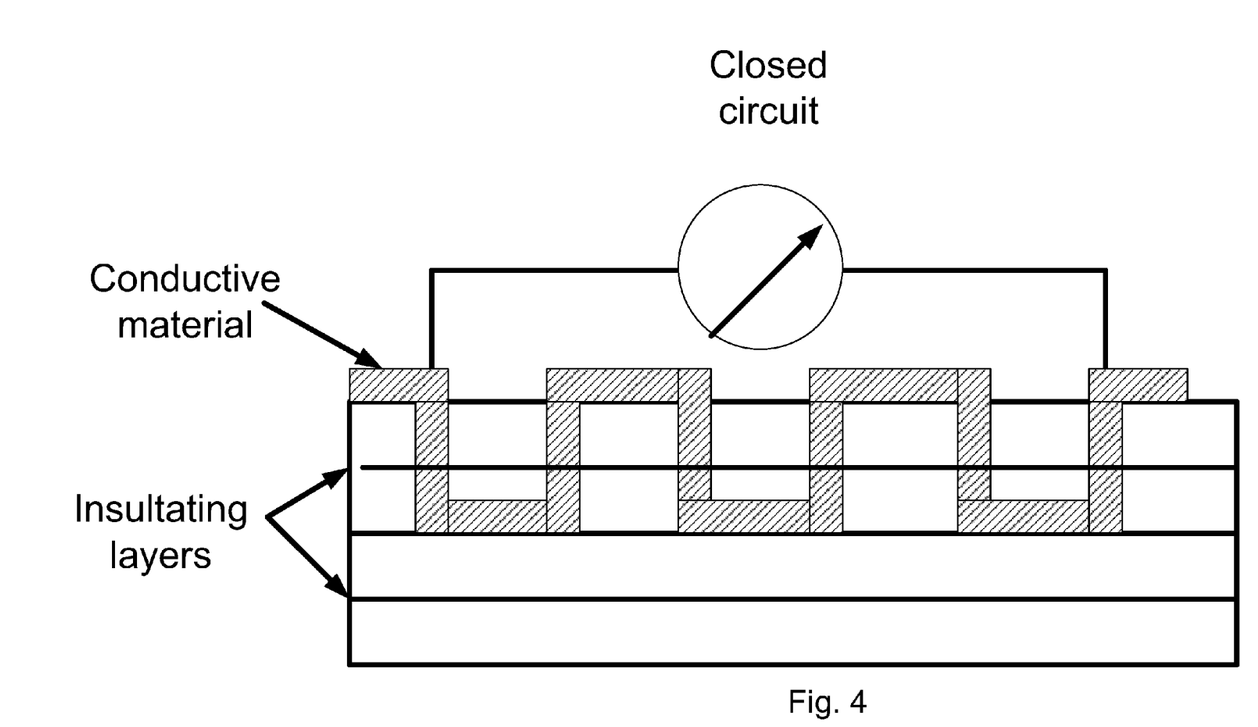
FIG. 4 is a schematic view of an exemplifying embodiment according to the present invention.

Connection was confirmed by measuring a short circuit between the upper and lower layer endpoints that are shown in FIG. 4. The current has gone alternating through the upper and lower layer through six vias.

Example 2

A machine for layer manufacturing was built. It consists of a table with linear actuators (NSK and HIWIN) that can move a stage in x-y-z directions. The movable stage is controlled with a PLC controller (Beijer).

The movable stage is fitted with a slot die (Premier Dies) fed by a ceramic suspension under pressure with a precision pump (such as a precision gear pump). The ceramic suspension is similar to example 1 but the solids concentration was adjusted to a viscosity suitable for the slot die.

Inkjet heads (HP) with a drive electronic (Megatech Electronic) was fixed to the stage to be able to print both a temporary latex binder and a hydrophobic liquid.

Dispensers were also fitted to the movable stage and filled with conductive paste.

A computer was programmed to control the slot die through the PLC and to transfer printing information to drive printing electronic for each layer. The movable stage was then raised before deposition of the next layer.

This machine was used to building 3D conductive vias in ceramic packaging structure.

Figure 5:
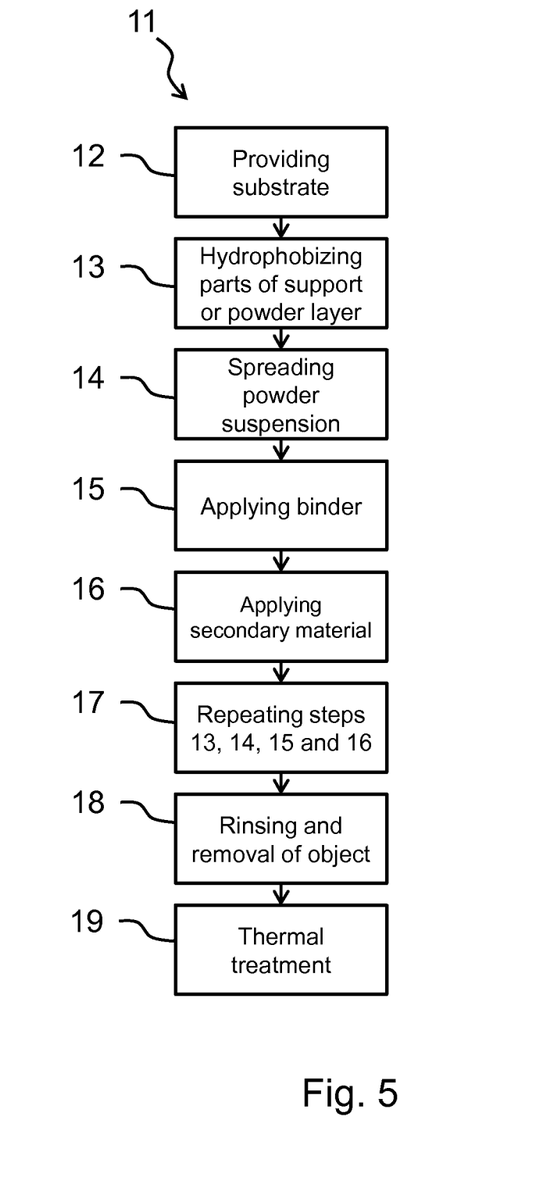
FIG. 5 is a schematic flow chart of an embodiment of the method according to the present invention.

With reference to FIG. 1, FIG. 2 and FIG. 5, embodiment objects 1 manufactured using exemplifying method 11 are illustrated. As shown, the exemplifying embodiment of the method 11 comprises:

providing a flat substrate as a platform forming a support 2 for building the object 1, indicated by block 12 in FIG. 5, hydrophobizing selected parts of a flat substrate, such as the powder layer 4, 4a, 4b of water-based powder suspension, or the platform forming the support 2, by applying a hydrophobic solution, such as 3a or 3b, indicated by block 13 in FIG. 5;

spreading a water-based powder suspension 4a or 4b comprised of particles with a size below 5 (five) μm in a layer with a thickness below 50 (fifty) μm, indicated by block 14 in FIG. 5;

applying a binder 5 to the parts of the powder layer that should be retained in the shaped powder body, indicated by block 15 in FIG. 5;

applying one or more secondary materials 6a as powder suspensions or powder pastes to the gaps in the layer created by the hydrophobic repulsion of the water-based suspension, indicated by block 16 in FIG. 5;

repeatedly adding powder layers 4a, 4b, 4c, etc., hydrophobic areas 3a and 3b, binders 5a, 5b, and 5c and secondary materials corresponding to secondary material 6a, as above to build a powder body of the desired shape and size, indicated by block 17 in FIG. 5;

rinsing or clearing the object from lose powder and removing the object from the support 2, indicated by block 18 in FIG. 5; and performing thermal treatment to remove the binder and sinter the powder object to a solid body, indicated by block 19 in FIG. 5.

It is noted that, with reference to FIG. 2, it is illustrated that selected part of the powder layer 4a and 4b forms the flat substrate which is/are hydrophobized by applying a hydrophobic solutions 3a and/or 3b. However, the hydrophobic solution may also be applied directly on the platform forming the support 2, wherein the platform forming the support 2 forms the flat substrate in the hydrophobizing step.

It should be noted that the invention has mainly been described above with reference to a few embodiments. However, as is readily appreciated by a person skilled in the art, other embodiments than the ones disclosed above are equally possible within the scope of the invention, as defined by the appended patent claims.

It is further noted that, in the claims, the word "comprising" does not exclude other elements or steps, and the indefinite article "a" or "an" does not exclude a plurality. A single apparatus or other unit may fulfill the functions of several items recited in the claims. The mere fact that certain features or method steps are recited in mutually different dependent claims does not indicate that a combination of these features or steps cannot be used to an advantage.

The invention claimed is:

1. A method for additive layer manufacturing of objects comprised of a plurality of materials with free-form capability for each material, the method including the steps of:

providing a flat substrate as a platform, forming a support for building a powder object;

hydrophobizing selected parts of the flat substrate by applying a hydrophobic solution, forming at least one hydrophobic area;

spreading a water-based powder suspension comprised of particles with a size less than 5 micrometers (μm) in a powder layer with a thickness less than 50 μm;

applying a binder to parts of the powder layer that are retained in the powder object;

applying at least one of a powder suspension or a powder paste as a secondary material to gaps in the powder layer, wherein the gaps are created by a hydrophobic repulsion of the water-based powder suspension;

repeatedly adding other powder layers, other hydrophobic areas, the binder, and at least one of the secondary materials to build the powder object of a desired shape and size;

clearing loose powder from the powder object; and performing thermal treatment to remove the binder from the powder object and to sinter the powder object to a solid body.

2. The method according to claim 1 wherein gaps in the powder layers are selectively filled with a sacrificial material that leaves at least one of a cavity or a channel in the solid body.

3. The method according to claim 1 wherein the powder suspension is deposited in layers by at least one of a doctor blade, slot die, or extrusion method, and wherein at least one of the hydrophobic solution or the binder is deposited by inkjet printing, and the secondary materials are deposited by at least one of dispensing or inkjet printing.

4. The method according to claim 1, wherein the hydrophobic solution is at least one of a solution or a dispersion of at least one of fluorocarbons or silicones.

5. The method according to claim 1, wherein the powder suspension includes at least one of a ceramic or a hard metal powder.

6. The method according to claim 1, wherein additional functionally is added by including at least one of a dielectric, resistive, semi-conductive, magnetic, or other functional material for at least one of sensing or actuating.

7. The method according to claim 1, wherein the method is used to create structures with at least one of conducting or insulating materials to create packaging for Microsystems.

8. The method according to claim 1, wherein the method is used to create at least one of implants or dental replacements.

9. The method according to claim 1, wherein the method is used to create tools for at least one of grinding or cutting.

10. The method according to claim 1, wherein the method is used to create a mechanical precision part.

11. The method according to claim 1, wherein the method is used to create at least one of a channel or a cavity in a ceramic material with a metalized surface for use as a wave guide for microwaves.

12. The method according to claim 1, wherein the method is used to create at least one of a channel and or a cavity in a ceramic material with a metalized surface for transport of fluid.

13. The method according to claim 1, wherein the method is used to create an optical waveguide.

14. The method according to claim 13, wherein the waveguide is created in or on top of a ceramic material.

15. The method according to claim 1, wherein the steps further include removing the powder object from the support.

16. The method according to claim 2 wherein the powder suspension is deposited in layers by at least one of a doctor blade, slot die, or extrusion method, and wherein at least one of the hydrophobic solution or the binder is deposited by inkjet printing, and the secondary materials are deposited by at least one of dispensing or inkjet printing.

17. The method according to claim 2, wherein the hydrophobic solution is at least one of a solution or a dispersion of at least one of fluorocarbons or silicones.

18. The method according to claim 2, wherein the powder suspension includes at least one of a ceramic or a hard metal powder.

19. A method for additive layer manufacturing of objects comprised of a plurality of materials with free-form capability for each material, the method including the steps of:
- providing a flat substrate as a platform, forming a support for building a powder object;
- hydrophobizing selected parts of the flat substrate by applying a hydrophobic solution, forming at least one hydrophobic area;
- spreading a water-based powder suspension comprised of particles with a size less than 5 micrometers (μm) in a powder layer with a thickness less than 50 μm;
- applying a binder to parts of the power layer that are retained in the powder object;
- applying at least one of a powder suspension or a powder paste as a secondary material to gaps in the powder layer, wherein the gaps are created by a hydrophobic repulsion of the water-based powder suspension;
- repeatedly adding other powder layers, other hydrophobic areas, the binder, and at least one of the secondary materials to build the powder object of a desired shape and size;
- rinsing loose powder from the powder object; and
- performing thermal treatment to remove the binder from the powder object and to sinter the powder object to a solid body.

20. The method according to claim 19, wherein the steps further include removing the powder object from the support.

* * * * *